United States Patent
Caborn et al.

(10) Patent No.: US 7,468,074 B2
(45) Date of Patent: Dec. 23, 2008

(54) LIGAMENT FIXATION USING GRAFT HARNESS

(75) Inventors: David N. Caborn, Louisville, KY (US); Gregory Guederian, Naples, FL (US)

(73) Assignee: Arthrex, Inc., Naples, FL (US)

( * ) Notice: Subject to any disclaimer, the term of this patent is extended or adjusted under 35 U.S.C. 154(b) by 556 days.

(21) Appl. No.: 10/975,379

(22) Filed: Oct. 29, 2004

(65) Prior Publication Data

US 2006/0095130 A1    May 4, 2006

(51) Int. Cl.
*A61F 2/08* (2006.01)
(52) U.S. Cl. .................................. 623/13.14
(58) Field of Classification Search .............. 623/13.11, 623/13.12, 13.13, 13.14, 13.19, 13.2; 606/65, 606/72, 73, 301
See application file for complete search history.

(56) References Cited

U.S. PATENT DOCUMENTS

| | | | |
|---|---|---|---|
| 6,562,043 B1 | 5/2003 | Chan | |
| 6,623,524 B2 | 9/2003 | Schmieding | |
| 6,712,849 B2 * | 3/2004 | Re et al. ................... | 623/13.14 |
| 6,878,166 B2 * | 4/2005 | Clark et al. ............... | 623/13.12 |
| 6,887,271 B2 * | 5/2005 | Justin et al. .............. | 623/13.14 |
| 7,063,724 B2 * | 6/2006 | Re et al. ................... | 623/13.14 |
| 2002/0165611 A1 * | 11/2002 | Enzerink et al. .......... | 623/13.11 |
| 2003/0065390 A1 * | 4/2003 | Justin et al. .............. | 623/13.14 |
| 2003/0130735 A1 * | 7/2003 | Rogalski .................. | 623/13.15 |
| 2003/0171810 A1 * | 9/2003 | Steiner ..................... | 623/13.14 |
| 2003/0171811 A1 * | 9/2003 | Steiner et al. ............. | 623/13.17 |
| 2003/0191530 A1 * | 10/2003 | Sklar ........................ | 623/13.14 |
| 2004/0030385 A1 * | 2/2004 | Steiner ..................... | 623/13.14 |
| 2004/0172034 A1 * | 9/2004 | Re et al. ........................ | 606/73 |
| 2004/0267318 A1 * | 12/2004 | Boucher et al. ............. | 606/232 |
| 2004/0267361 A1 * | 12/2004 | Donnelly et al. .......... | 623/13.14 |
| 2005/0010289 A1 * | 1/2005 | McKernan et al. ....... | 623/13.14 |
| 2005/0071004 A1 * | 3/2005 | Re et al. ................... | 623/13.11 |
| 2005/0159812 A1 * | 7/2005 | Dinger et al. ............. | 623/13.14 |
| 2005/0171603 A1 * | 8/2005 | Justin et al. ............... | 623/13.14 |
| 2005/0203623 A1 * | 9/2005 | Steiner et al. ............. | 623/13.14 |
| 2006/0030940 A1 * | 2/2006 | Schmieding .............. | 623/13.14 |
| 2006/0142769 A1 * | 6/2006 | Collette ........................ | 606/73 |
| 2006/0265064 A1 * | 11/2006 | Re et al. ................... | 623/13.14 |

* cited by examiner

*Primary Examiner*—Thomas J Sweet
(74) *Attorney, Agent, or Firm*—Dickstein Shapiro LLP

(57) ABSTRACT

A graft harness for securing a ligament in a bone tunnel takes the form of a shaped plug having a proximal end and a distal end. A radial groove is formed in the distal end of the plug which accepts a looped ligament graft. A suture passageway formed through the plug transverse to the groove accepts a length of suture. The proximal end of the plug features a concave configuration adapted to accept the distal end of an interference screw. A ligament graft is secured in a bone tunnel using the graft harness by seating the looped graft within the groove to form a harness/graft construct, passing a length of suture through the suture passageway, and drawing the harness/graft construct into the tunnel using the length of suture looped through the suture passageway. The graft is secured primarily using an interference screw which engages the concave proximal end of the harness. The harness provides secondary fixation of the graft in the bone tunnel.

11 Claims, 5 Drawing Sheets

1

LIGAMENT FIXATION USING GRAFT HARNESS

BACKGROUND OF THE INVENTION

1. Field of the Invention

The present invention relates to apparatus and methods for ligament fixation, and more particularly to techniques using a graft harness for secondary fixation of soft tissue ligament grafts in a femoral tunnel.

2. Description of the Related Art

When soft tissues, such as tendons or ligaments, tear or detach from bone, it is often necessary to reconnect the structures surgically. Cruciate ligament reconstruction is routinely performed by creating femoral and tibial tunnels into which ligament grafts are secured. Various graft types are used to replace the native cruciate ligament. Biomechanical studies have shown that an anatomic double-bundle cruciate ligament reconstruction is superior in restoring normal knee laxity compared with conventional single-bundle isometric reconstructions. An example of cross pin fixation of a looped, double bundle graft is shown in U.S. Pat. No. 6,623,524 to Schmieding, the disclosure of which is incorporated herein by reference. Improved methods for installing and securing double-bundle cruciate ligament grafts could enhance reconstruction results.

BRIEF SUMMARY OF THE INVENTION

The invention provides ligament graft fixation using a graft harness. The harness takes the form of a shaped plug having a radial groove at its distal end which accepts a looped ligament graft. A suture passageway formed through the plug transverse to the groove accepts a length of suture which is used to draw the harness with the ligament graft into the tunnel. The graft is introduced to the bone tunnel by seating the looped graft within the groove of the harness and drawing the harness/graft construct into the tunnel using the length of suture looped through the suture passageway and drawn out through an opening formed at the top of the tunnel. The proximal end of the plug has a concave configuration which accepts the distal end of an interference screw. The graft is secured femorally using the interference screw, which engages the concave proximal end of the harness. The harness provides secondary fixation within the femoral tunnel.

Other features and advantages of the present invention will become apparent from the following description of the invention which refers to the accompanying drawings.

DETAILED DESCRIPTION OF THE INVENTION

Figure 1:
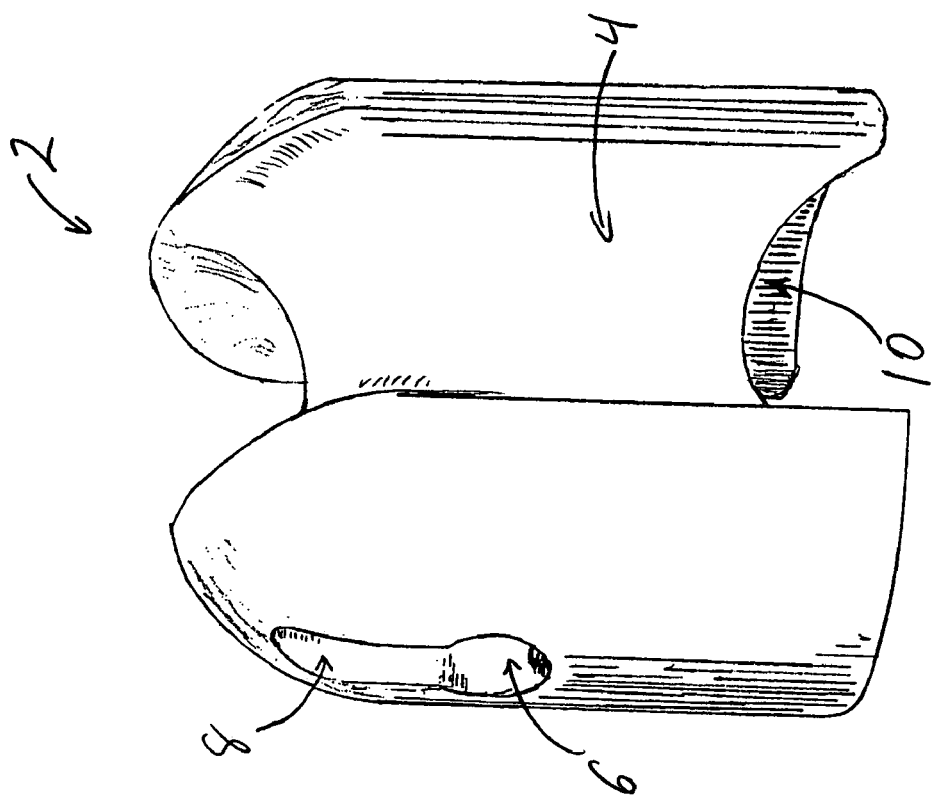
FIG. 1 illustrates a graft harness according to the present invention showing a perspective view in elevation.

Referring initially to FIG. 1, a preferred embodiment of a graft harness 2 according to the present invention is shown. The harness 2 preferably takes the form of a cylindrically-shaped plug about 7 mm in diameter and 8 mm in length, although the harness 2 can be provided in multiple sizes. The device is made from a biocompatible material, and preferably from bioabsorbable materials, bone, or synthetic bone.

The harness 2 features a radial groove 4 which accepts a looped ligament graft. Radial groove 4 originates on opposite sides of the underside of the plug bilaterally to meet at the apex, as described further below.

Figure 2:
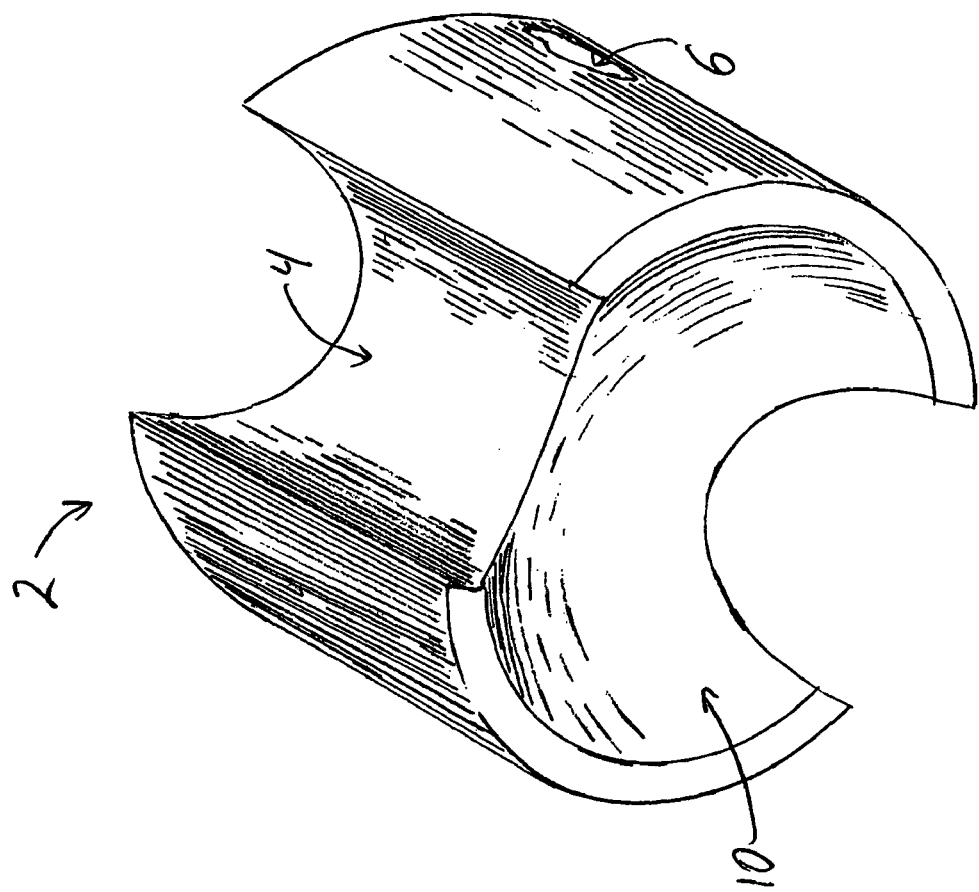
FIG. 2 illustrates the graft harness of FIG. 1 showing a perspective view taken from a proximal end of the harness.

As shown in FIG. 2, the underside 10 of the harness 2 has a concave configuration for accepting the end of an interference screw. This spherical impression is formed to complement adjoining screw geometry, and could have other configurations.

Figure 4:
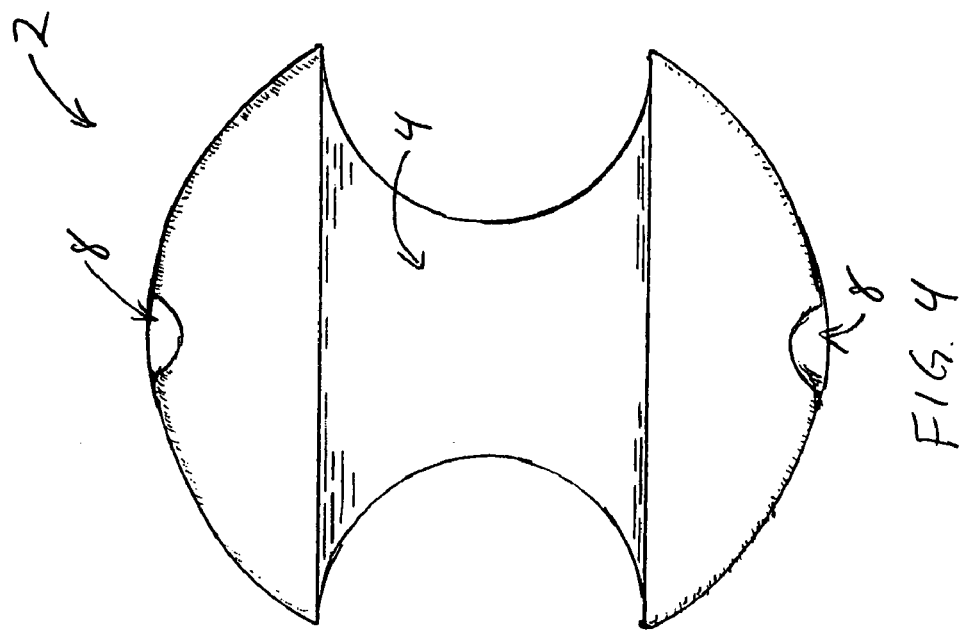
FIG. 4 illustrates the graft harness of FIG. 1 showing a plan view.
Figure 3:
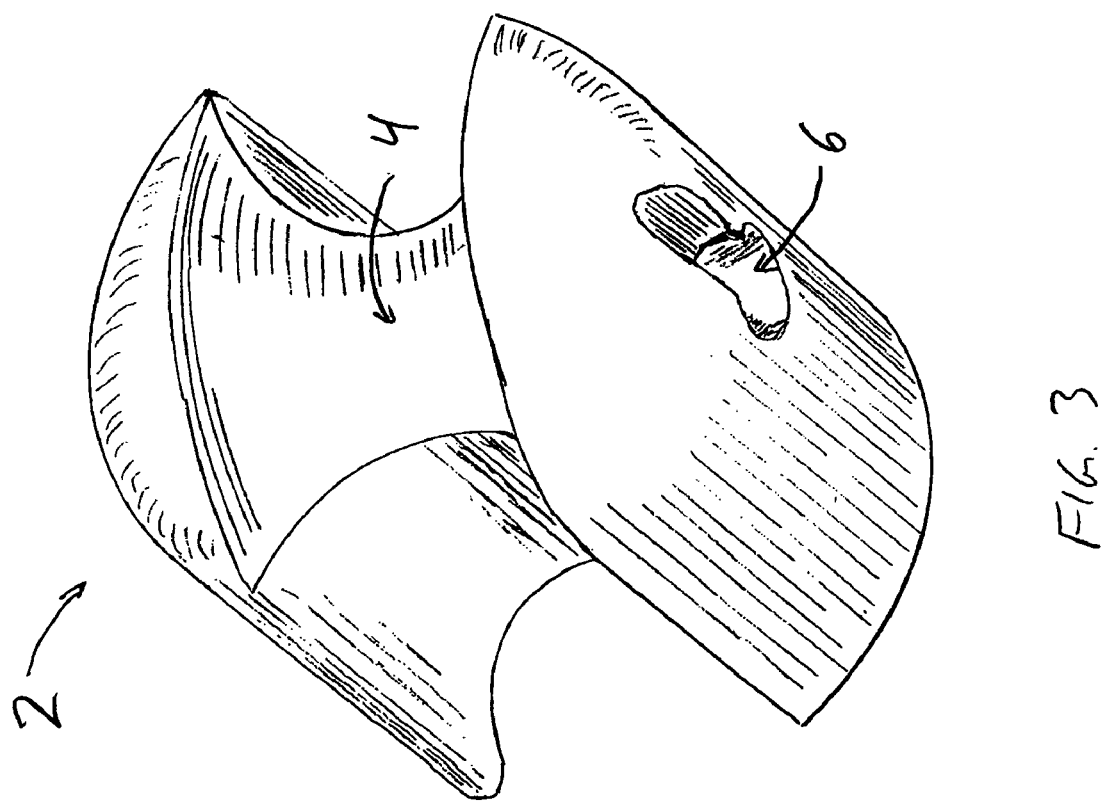
FIG. 3 illustrates the graft harness of FIG. 1 showing a perspective view taken from a distal end of the harness.

Referring to FIGS. 3 and 4, the harness 2 is substantially conical distally. A transverse through hole 6, perpendicular to radial groove 4, accommodates a suture strand having a size up to #5 in diameter. Passageway 6, shown as a through hole in FIG. 1, also can be formed as a slot to accommodate additional sutures and sutures of larger size. Longitudinal slots 8 intersect through hole 6 bilaterally, which allows for the length of suture to rest within the device, reducing the likelihood of suture slippage or migration during installation of the harness into the bone tunnel. Suture looped through passageway 6 resting within the notches 8 also is protected from potentially damaging contact with bone tunnel walls.

Figure 5:
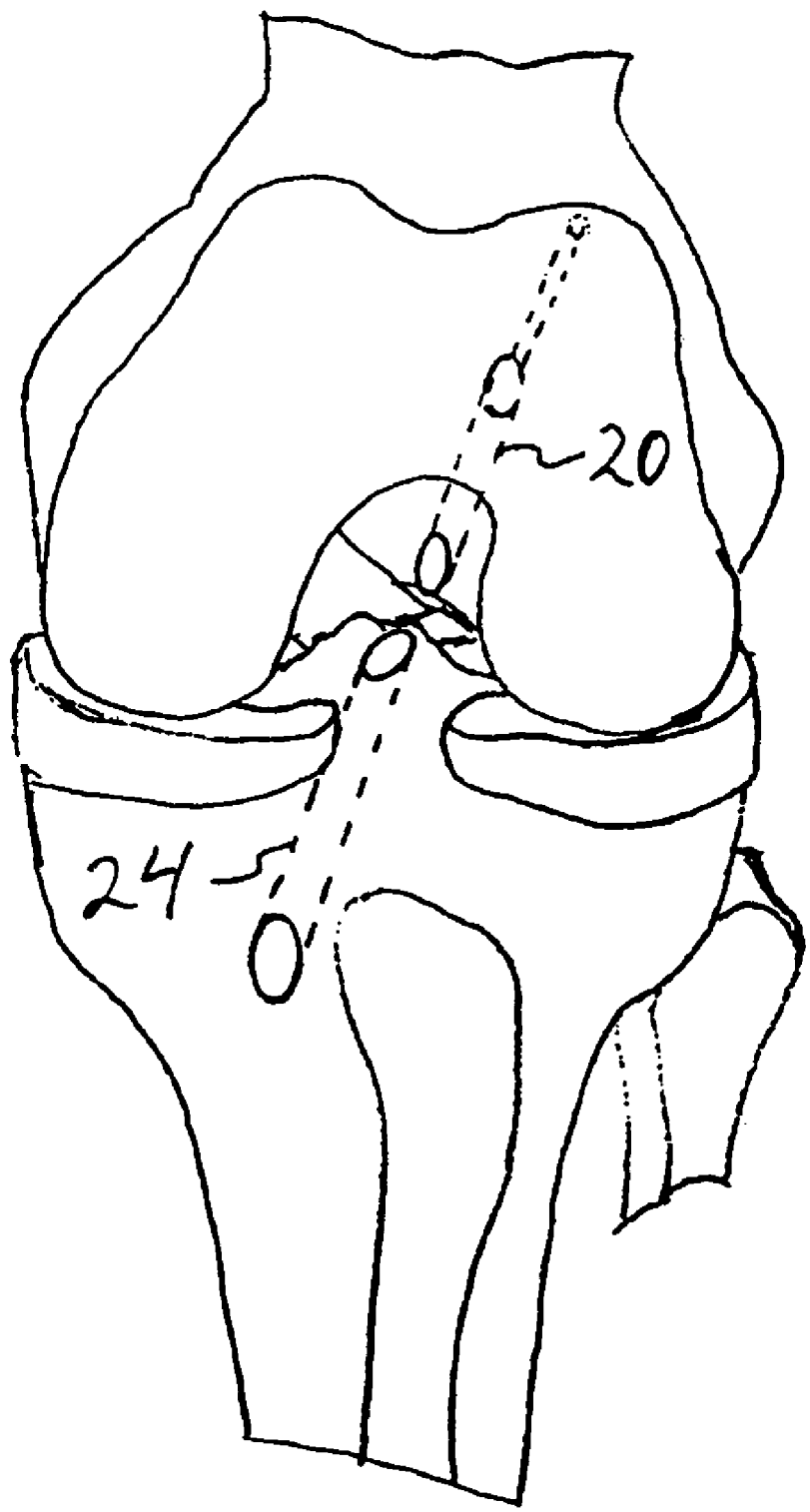
FIG. 5 is a schematic anterior view of a left knee showing tunnels formed according to the present invention.
Figure 6:
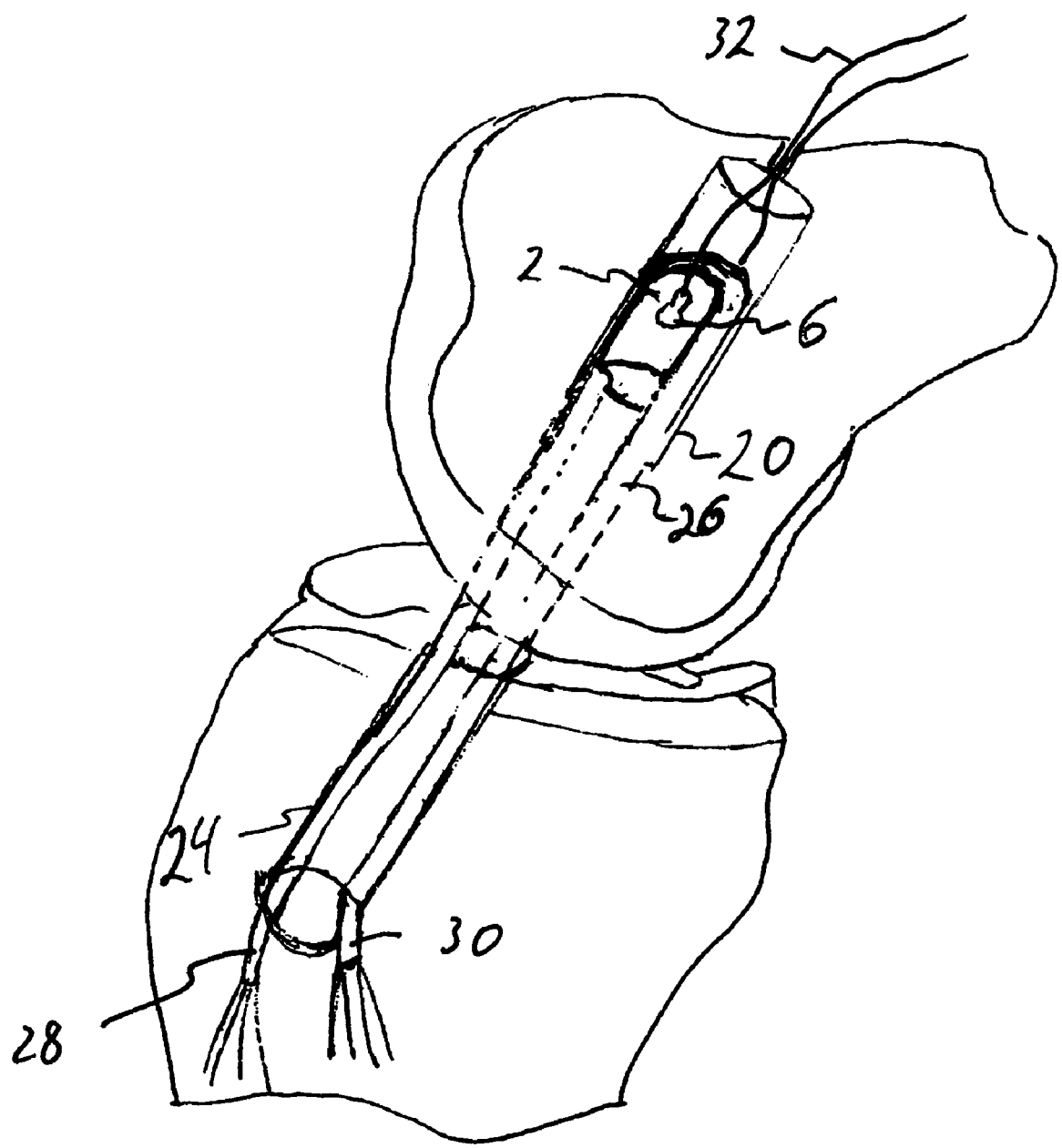
FIG. 6 is a partially cut-away side view of the knee of FIG. 5 showing installation of a ligament graft using a graft harness according to the present invention.

Referring to FIGS. 5 and 6, a preferred method of ligament fixation according to the present invention involves preparing a femoral tunnel 20 and a tibial tunnel 24 in the usual manner. A soft tissue graft 26 is looped and draped over the harness 2 to form a harness/graft construct. The radial groove 4 of harness 2 secures the looped ligament graft against transverse slippage out of the groove 4. The radial groove 4 has an arcuate cross-section which securely holds the ligament graft 26 even if some misalignment of harness 2 presents within the tunnel 20. In addition, the smooth surfaces of harness 2 that form recess 4 support and spread the ligament graft bilaterally without trauma from acute edges or suture which could cut or fray the graft and reduce the strength and longevity of the reconstruction.

The harness/graft construct is depicted in FIG. 6 as having been inserted within femoral tunnel 20 and is in the process of being seated in femoral tunnel 20. Prior to installation, individual legs 28, 30 of the graft 26 are separated and placed within the recesses of groove 4 on either side of the harness 2. Tension is applied to the legs 28, 30 of the graft 26 to seat the graft 26 within the distal and longitudinal portions of groove 4. A single suture 32 is passed through the through hole 6 of harness 2. The free ends of suture 32 are passed into and out the top of the femoral tunnel 20. The suture 32 is used to draw the harness 2 with the graft 26 into the femoral tunnel 20.

Figure 7:
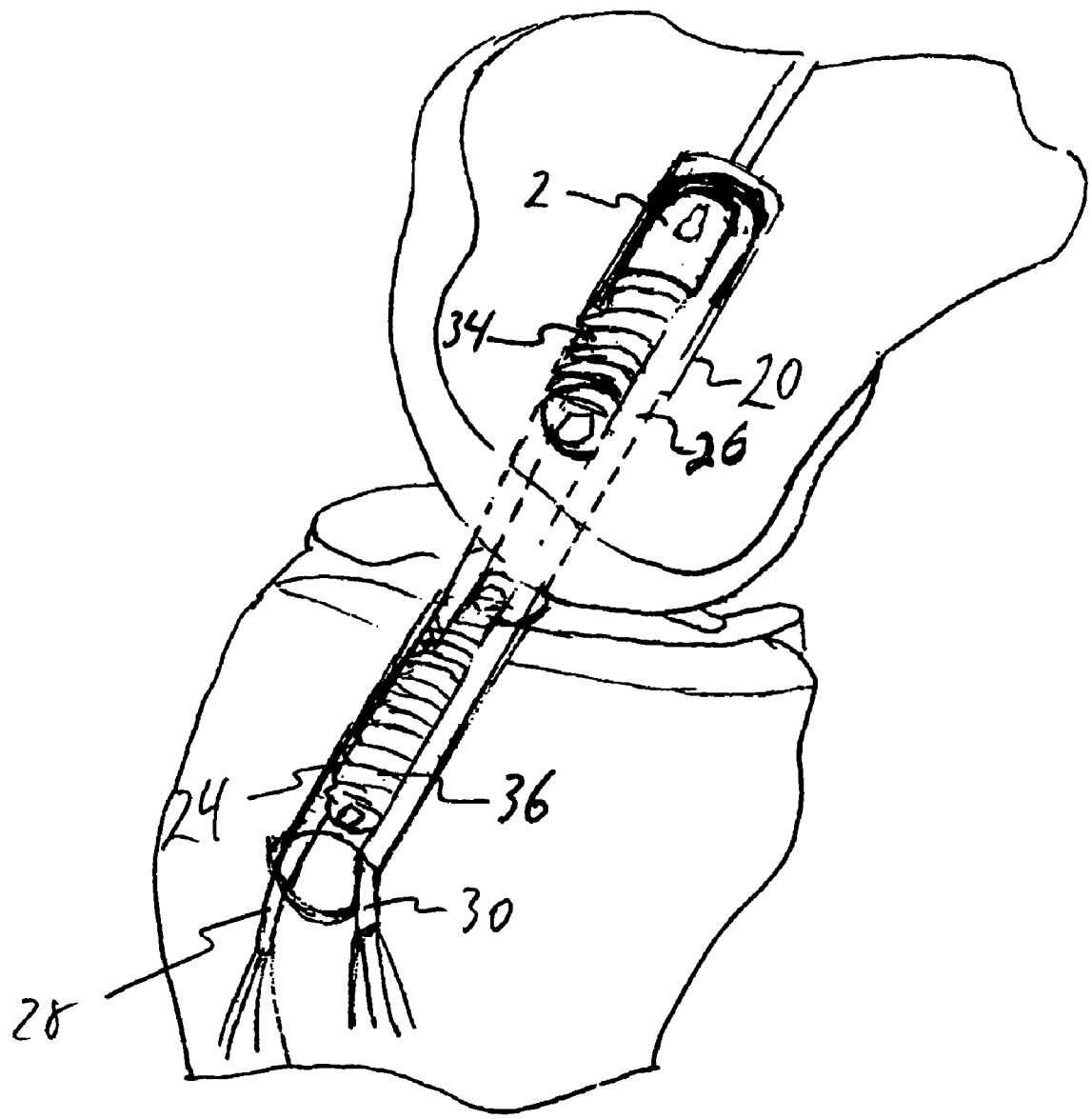
FIG. 7 is a partially cut-away side view of the knee of FIG. 5 showing interference screw fixation of the ligament graft using the graft harness according to the present invention.

Referring to FIG. 7, the harness/graft construct is shown fully seated in bone tunnel 20. Legs 28, 30 of the graft bundle 26 are separated bilaterally, and an interference screw 34 is introduced centrally and advanced until resistance is observed in meeting with the proximal end of the graft harness 2. As noted above, the underside 10 of the proximal end of harness 2 has a concave spherical configuration, for example, for accepting the end of the interference screw 34. This concavity is formed to complement interference screw geometry, and prevents slippage between the harness 2 and the interference screw 34. The concavity is configured to accommodate possible misalignment of the harness 2 within the tunnel 20 to insure that a non-slipping connection is made between the harness 2 and the interference screw 34.

Alternatively, the legs 28 and 30 can be combined to form a bundle with the interference screw 34 placed collateral to the bundle within the tunnel. A second interference screw 36 secures the graft in the tibial tunnel 24. The legs 28, 30 of graft 26 preferably are oriented to approximate the anatomical orientation of the original tendon.

Tunnel fixation also can be accomplished using methods disclosed in co-pending patent application no., based on U.S. Prov. No. 60/515,429), of common assignment with the present application, and incorporated herein by reference in its entirety. The fixation method described in patent application no. relates to the use of a notcher, burr, or rasp to widen the tunnels 20, 24 into a substantially oval shape. The tunnel shape attained is sufficiently wide to accommodate a fixation implant installed between the two strands of the replacement graft inserted into the tunnels. The prepared double-bundle graft is passed through the tibial tunnel and into the femoral tunnel. A femoral fixation implant, preferably in the form of a threaded screw, is placed between the two ligament strands 28, 30 to anatomically spread the graft 26, approximating the double bundle biomechanical function of the double bundle native ligament whereby one ligament strand tensions in knee extension and the other ligament strand tensions in knee flexion.

A tibial implant 36 similarly is positioned between the graft strands 28, 30 during tibial fixation to spread the strands into an anatomical orientation in the preferably oval tibial tunnel 24, to closely approximate the anatomical double bundle function of the native ligament. Insertion preferably uses a retrograde method, as described in U.S. Pat. No. 6,461, 373 to Wyman et al., referenced above and incorporated herein by reference.

As can be seen from the figures, in the completed reconstruction ligament graft 26 is looped over harness 2 in groove 4 and secured with interference screw 34. The construct is formed with the ligament graft 26 looped around harness 2 on a side opposite to that of interference screw 34. No suture need be attached between the harness 2 and ligament graft 26 in order to achieve interference fixation. The recessed groove 4 and the concave underside 10 of harness 2 prevent slippage between the ligament graft 26 and the harness 2, and the harness 2 and the interference screw 34, respectively.

The methods and devices of the present invention can be applied to anterior or posterior cruciate ligament reconstruction in the knee, for example. The methods and devices also can be adapted easily by one of skill in the art for ligament reconstruction in a variety of joints, including those in humans and otherwise.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Additions, deletions, substitutions, and other modifications can be made without departing from the spirit or scope of the present invention. Accordingly, the invention is not to be considered as limited by the foregoing description but is only limited by the scope of the appended claims.

What is claimed is:

1. A graft harness comprising:
   a shaped plug having a proximal end, a distal end, an apex and two lateral opposing sides, wherein the proximal end is provided with a spherical concavity;
   a radial groove formed in the plug which accepts a looped ligament graft, the radial groove originating on opposite sides of an underside of the plug bilaterally, to meet at the apex, the radial groove comprising a recess on each of the two lateral opposing sides of the plug so that individual legs of the looped ligament graft are placed within each recess on each opposing side of the groove; and
   a suture passageway formed through the plug transverse to the groove.

2. A graft harness as in claim 1, wherein the spherical concavity accepts an end of an implant.

3. A graft harness as in claim 2, wherein the concavity is provided to be complementary to an interference screw.

4. A graft harness as in claim 1, wherein the shaped plug is cylindrical.

5. A graft harness as in claim 1, wherein the suture passageway further includes a rounded notch formed distally to provide a relief for suture looped through the suture passageway.

6. A graft harness as in claim 1, wherein the recess has an arcuate cross-section.

7. A method of securing a ligament graft in a bone tunnel using a graft harness, the graft harness comprising a shaped plug having a proximal end and a distal end, a radial groove formed in the plug which accepts a looped ligament graft, the radial groove comprising a recess on each of two lateral opposing sides of the shaped plug, and a suture passageway formed through the plug transverse to the groove, the method comprising the steps of:
   seating the looped graft within both of the recesses on the lateral opposing sides of the groove to form a harness/graft construct;
   passing a length of suture through the suture passageway;
   drawing the harness/graft construct into the tunnel using the length of suture looped through the suture passageway; and
   installing an interference screw which engages a spherical concavity at the proximal end of the graft harness.

8. A method as in claim 7, wherein the recess has an arcuate cross-section.

9. A method of repairing a cruciate ligament comprising:
   forming femoral and tibial bone tunnels in a cruciate-deficient knee;
   looping a ligament graft over a graft harness, the harness being provided as a shaped plug having a proximal end and a distal end, a radial groove formed in the plug which accepts the looped ligament graft, the radial groove comprising a recess on each of two lateral opposing sides of the shaped plug, a suture passageway formed through the plug transverse to the groove, and a concavity formed in the proximal end of the plug for accepting an interference screw;
   seating the looped graft within both of the recesses on the lateral opposing sides of the groove to form a harness/graft construct;
   passing a length of suture through the suture passageway in the harness;
   drawing the harness/graft construct into the femoral tunnel using the length of suture looped through the suture passageway; and
   installing an interference screw in the femoral tunnel which engages the concavity in the proximal end of the harness.

10. A method as in claim 9, further comprising the step of installing an interference screw which secures the graft in the tibial tunnel.

11. A method as in claim 9, wherein the recess has an arcuate cross-section.

* * * * *